US011576590B2

(12) United States Patent
Tao et al.

(10) Patent No.: US 11,576,590 B2
(45) Date of Patent: Feb. 14, 2023

(54) IMAGING-BASED SPIROMETRY SYSTEMS AND METHODS

(71) Applicant: Arizona Board of Regents on Behalf of Arizona State University, Tempe, AZ (US)

(72) Inventors: Nongjian Tao, Fountain Hills, AZ (US); Chenbin Liu, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 782 days.

(21) Appl. No.: 16/490,749

(22) PCT Filed: Mar. 13, 2018

(86) PCT No.: PCT/US2018/022252
§ 371 (c)(1),
(2) Date: Sep. 3, 2019

(87) PCT Pub. No.: WO2018/170009
PCT Pub. Date: Sep. 20, 2018

(65) Prior Publication Data
US 2020/0000370 A1    Jan. 2, 2020

Related U.S. Application Data

(60) Provisional application No. 62/470,651, filed on Mar. 13, 2017.

(51) Int. Cl.
*A61B 5/091*       (2006.01)
*G06T 7/00*        (2017.01)
(Continued)

(52) U.S. Cl.
CPC .............. *A61B 5/091* (2013.01); *A61B 5/004* (2013.01); *A61B 5/087* (2013.01); *A61B 5/1128* (2013.01);
(Continued)

(58) Field of Classification Search
None
See application file for complete search history.

(56) References Cited

U.S. PATENT DOCUMENTS 7,785,001 B2   8/2010   Tao et al.
8,545,683 B2   10/2013  Tao et al.
(Continued)

FOREIGN PATENT DOCUMENTS

WO   2009064985 A1   5/2009
WO   2010030874 A1   3/2010
(Continued)

OTHER PUBLICATIONS

Search Report from corresponding Application No. PCT/US2018/022252 (WO 2018/170009 A1).
(Continued)

*Primary Examiner* — Frank S Chen
(74) *Attorney, Agent, or Firm* — Polsinelli PC

(57) ABSTRACT

A spirometry system includes an imaging device configured to capture upper body movement images of a subject during inhalation and exhalation of the subject. The system further includes at least one controller configured to receive the captured images from the imaging device and, based upon the received images, determine at least one of an image-based spirometry flow-volume curve for the subject or an image-based spirometry parameter for the subject.

11 Claims, 5 Drawing Sheets

(51) Int. Cl.
  G06T 7/13       (2017.01)
  A61B 5/00       (2006.01)
  A61B 5/087      (2006.01)
  A61B 5/11       (2006.01)
  G06T 3/00       (2006.01)

(52) U.S. Cl.
  CPC .......... *G06T 3/0006* (2013.01); *G06T 7/0012* (2013.01); *G06T 7/13* (2017.01); *G06T 7/97* (2017.01)

(56) References Cited

U.S. PATENT DOCUMENTS

| | | | |
|---|---|---|---|
| 8,668,874 | B2 | 3/2014 | Tao et al. |
| 9,347,932 | B2 | 5/2016 | Tao et al. |
| 9,581,561 | B2 | 2/2017 | Tao et al. |
| 9,909,993 | B2 | 3/2018 | Tao et al. |
| 9,931,055 | B2 | 4/2018 | Forzani et al. |
| 10,078,074 | B2 | 9/2018 | Tsow et al. |
| 10,078,795 | B2 | 9/2018 | Tao et al. |
| 10,143,401 | B2 | 12/2018 | Tao et al. |
| 10,209,232 | B2 | 2/2019 | Forzani et al. |
| 10,401,298 | B2 | 9/2019 | Tao et al. |
| 10,413,226 | B2 | 9/2019 | Tao et al. |
| 10,663,442 | B2 | 5/2020 | Forzani et al. |
| 10,740,650 | B2 | 8/2020 | Tao et al. |
| 2010/0111386 | A1 | 5/2010 | El-Baz |
| 2012/0046568 | A1 | 2/2012 | Soatto et al. |
| 2013/0324830 | A1 | 12/2013 | Bernal et al. |
| 2014/0276104 | A1 | 9/2014 | Tao et al. |
| 2015/0265187 | A1 | 9/2015 | Bernal et al. |
| 2018/0140255 | A1 | 5/2018 | Tao et al. |
| 2019/0082972 | A1 | 3/2019 | Tao et al. |
| 2019/0094146 | A1 | 3/2019 | Tao et al. |
| 2019/0239761 | A1 | 8/2019 | Tao et al. |
| 2020/0022628 | A1 | 1/2020 | Tao et al. |

FOREIGN PATENT DOCUMENTS

| | | | |
|---|---|---|---|
| WO | 2010141610 | A1 | 12/2010 |
| WO | 2012047792 | A2 | 4/2012 |
| WO | 2013019843 | A2 | 2/2013 |
| WO | 2014052741 | A1 | 4/2014 |
| WO | 2014116604 | A1 | 7/2014 |
| WO | 2015102902 | A2 | 7/2015 |
| WO | 2017156084 | A2 | 9/2017 |
| WO | 2018057753 | A1 | 3/2018 |
| WO | 2019136097 | A1 | 7/2019 |

OTHER PUBLICATIONS

Vibot Day, Erasmus Mundus Masters in Vision and Robotics, published 2010. [retrieved on May 21, 2018 (May 21, 2018)] Retrieved from the internet <URL:vibot.udg.edu/?download=proceedingsVIBOTDay2010_final.pdf> (p. 64, col. 1; p. 76, col. 1 to p. 77, col. 2).

Chon, et al., Estimation of respiratory rate from photoplethysmogram data using time-frequency spectral estimation, IEEE Trans. Biomed. Eng. 56(8), 2054-2063 (2009).

Comaniciu, et al., Real-time tracking of non-rigid objects using mean shift, in Proc. IEEE Conf. on Computer Vision and Pattern Recognition, vol. 2, pp. 142-149 (2000).

Droitcour, et al., Signal-to-noise ratio in Doppler radar system for heart and respiratory rate measurements, IEEE Trans. Microwave Theory Tech. 57(10), 2498-2507 (2009).

Drummond et al., A video-based optical system for rapid measurements of chest wall movement, Physiol. Meas. 22(3), 489-503 (2001).

Huang, et al., Noninvasive respiratory monitoring system based on the piezoceramic transducer's pyroelectric effect, Rev. Sci. Instrum. 79(3), 35103 (2008).

Kenyon et al., Ribcage mechanics during quiet breathing and exercise in humans, J. Appl. Physiol. 83(4), 1242-1255 (1997).

Lai et al., Wireless sensing of human respiratory parameters by low-power ultrawideband impulse radio radar, IEEE Trans. Instrum. Meas. 60(3), 928-938 (2011).

Li et al., Tracking in low frame rate video: a cascade particle filter with discriminative observers of different life spans, IEEE Trans. Pattern Anal. Mach. Intell. 30(10), 1728-1740 (2008).

Lin, et al., Image-based motion-tolerant remote respiratory rate monitoring, IEEE Sens. J. 16(9), 3263-3271 (2016).

Lucas et al., An iterative image registration technique with an application to stereo vision, in Proc. of the 7th Int. Joint Conf. on Artificial Intelligence (IJCAI'81), vol. 81, No. 1, pp. 674-679 (1981).

Madhav et al., Robust extraction of respiratory activity from PPG signals using modified MSPCA, IEEE Trans. Instrum. Meas. 62(5), 1094-1106 (2013).

McCool et al., Estimates of ventilation from body surface measurements in unrestrained subjects, J. Appl. Physiol. 61(3), 1114-1119 (1986).

Menezes et al., Increased risk of exacerbation and hospitalization in subjects with an overlap phenotype: COPD-asthma, Chest 145(2), 297-304 (2014).

Miller et al., Standardisation of spirometry, Eur. Respir. J. 26(2), 319-338 (2005).

Mostov, et al., Medical applications of short-wave FM radar: remote monitoring of cardiac and respiratory motion, Med. Phys. 37(3), 1332-1338 (2010).

Murthy et al., Noncontact measurement of breathing function, IEEE Eng. Med. Biol. Mag. 25(3), 57-67 (2006).

Murthy et al., Thermal infrared imaging: a novel method to monitor airflow during polysomnography, Sleep 32(11), 1521-1527 (2009).

Plathow et al., Evaluation of chest motion and volumetry during the breathing cycle by dynamic MRI in healthy subjects: comparison with pulmonary function tests, Invest. Radiol. 39(4), 202-209 (2004).

Poh, et al., Advancements in non-contact, multiparameter physiological measurements using a webcam, IEEE Trans. Biomed. Eng. 58(1), 7-11 (2011).

Reyes et al., Tidal volume and instantaneous respiration rate estimation using a volumetric surrogate signal acquired via a smartphone camera, IEEE J. Biomed. Health Inf. 21(3), 764-777 (2016).

Shafiq et al., Surface chest motion decomposition for cardiovascular monitoring, Sci. Rep. 4, 5093 (2014).

Shao et al., Noncontact monitoring breathing pattern, exhalation flow rate and pulse transit time, IEEE Trans. Biomed. Eng. 61(11), 2760-2767 (2014).

Shi et al., Good features to track, in Proc. IEEE Computer Society Conf. on Computer Vision and Pattern Recognition (CVPR'94), pp. 593-600 (1994).

Tomasi et al., Detection and Tracking of Point Features, School of Computer Science, Carnegie Mellon University, Pittsburgh (1991).

Verkruysse, et al., Remote plethysmographic imaging using ambient light, Opt. Express 16(26), 21434-21445 (2008).

Wang, et al., A novel algorithm for remote photoplethysmography: spatial subspace rotation, IEEE Trans. Biomed. Eng. 63(9), 1974-1984 (2016).

Weng, et al., Video object tracking using adaptive Kalman filter, J. Visual Commun. Image Representation 17(6), 1190-1208 (2006).

U.S. Appl. No. 16/857,660, Tao et al., filed Apr. 24, 2020.

U.S. Appl. No. 16/959,646, Forzani et al., filed Jul. 1, 2020.

U.S. Appl. No. 16/984,842, Tao et al., filed Aug. 4, 2020.

IMAGING-BASED SPIROMETRY SYSTEMS AND METHODS

CROSS REFERENCE TO RELATED APPLICATIONS

This application claims priority to U.S. Patent Application No. 62/470,651 filed Mar. 13, 2017.

STATEMENT REGARDING: FEDERALLY SPONSORED RESEARCH

Not applicable.

BACKGROUND

The present disclosure relates generally to spirometry systems and methods.

Asthma and chronic obstructive pulmonary disease (COPD) are the most prevalent obstructive airway diseases that affect tens of millions of people in the US alone. The most common way to diagnose these diseases and reassess the progression of the diseases is spirometry, which measures how much a patient inhales, and how fast the patient exhales. In a typical spirometry test, a patient is instructed to exhale rapidly and forcefully into a mouthpiece connected to a physical spirometer (e.g., a device comprising one or more of a pressure transducer, an ultrasonic transmitter and/or receiver, or a water gauge) that, measures breath flow rate and volume. To ensure that all the air is inhaled into the spirometer for accurate flow measurement, the patient is also instructed to wear a nose clip, which leads to discomfort. For good hygiene, a disposal mouthpiece is used for each spirometry test. The needs of the spirometer, nose clip and mouthpiece contribute to factors that prevent widespread use of spirometry at home.

Efforts have been made to develop non-contact respiratory monitoring methods. Depending upon the monitoring principles, these methods can be divided into three general categories: thermal, photoplethysmography (PPG), and body movement detections. In thermal analyses, air temperature change associated with an exhaled breath near the mouth and nose regions of a subject is measured using an infrared imaging system. The temperature change can also be detected via the pyroelectric effect.

In PPG analyses, an embedded respiratory signal in the PPG signals is extracted. PPG measures the change of light absorption or reflection induced by the change of blood volume with each pulse. The movement of thoracic cavity affects the blood flow during breathing, which leads to a modulation in the PPG signal by the respiratory activity. Several PPG signal processing methods, including independent component analysis, principal component analysis, digital filtering and variable frequency complex demodulation have been proposed to remove noise in PPG and extract respiration-induced modulation in PPG.

In prior art body movement detection analyses, subtle chest movements induced by breathing are detected with different technologies, such as frequency-modulated radar wave and ultra-wide-band impulse radio radar. Optical imaging-based methods have been introduced to monitor respiratory activities. For example, a differential method to track the shoulder movement associated with breathing has been attempted. One method measures the intensity change of a chest wall. Another method applies an optical flow algorithm to detect respiratory activities. Both of these methods use low-cost cameras. More sophisticated three dimensional imaging with multi-camera and projector-camera setups have been used to track chest surface deformation during breathing. These prior art methods have been applied to monitoring various physiological parameters, including respiratory activities, but have not been successfully applied to non-contact spirometry. Rather, non-contact spirometry has typically required complex three-dimensional chest movement measurements, which are difficult and time consuming to acquire. For example, one prior method using three-dimensional chest movement measurement requires the use of retroreflective optical markers placed on the anterior upper body of a subject in a multi-row/multi-column grid along with multiple cameras placed in an approximately circular pattern around the subject to ensure that each optical marker placed on the chest is visible to at least three cameras for 3-D reconstruction of motion.

In light of the above, there is a need for image-based non-contact systems and methods for spirometry. Such systems and methods require accurate and quick measurement and determination of respiratory cycles over an extremely wide flow rate range, and the results in some instances need to be validated with real subjects.

SUMMARY

The present disclosure provides systems and methods for image-based spirometry that overcomes the aforementioned drawbacks and provides additional advantages.

In accordance with one aspect of the disclosure, a spirometry system includes an imaging device configured to capture upper body movement images of a subject during inhalation and exhalation of the subject. The system further includes at least one controller or computer that is configured to receive the captured images from the imaging device and based upon the received images, determine at least one of an image-based flow-volume spirometry curve for the subject or an image-based spirometry parameter for the subject.

In one aspect, the present disclosure provides a spirometry system comprising: an imaging device configured to capture images of a region of interest (ROI) in an upper body movement of a subject during inhalation and exhalation of a subject; and at least one controller in signal communication with the imaging device. The at least one controller is configured to: receive signals transmitted by the imaging device wherein the signals are representative of the captured images, process the received images, and determine an image-based flow-volume curve for the subject by: (i) identifying feature points in the ROI; (ii) registering adjacent frames in the ROI: (iii) determining transformation parameters; (iv) calibrating the movement of the ROI; and (v) determining the position of the ROI in a selected frame due to respiration as a function of a vertical component of the feature points in each frame. In the spirometry system, step (i) may comprise using a Harris corner detector to identify the feature points. In the spirometry system, step (ii) may comprise applying affine transformation to adjacent frames in the received images. In the spirometry system, step (iii) may comprise acquiring the transformation parameters from a vector produced by the dime transformation. In the spirometry system, step (iv) may comprise calibrating the movement by determining a ratio of a length of an identified feature point to a number of pixels corresponding to the feature point. In the spirometry system, step (v) may comprise calculating a summation of the vertical points of a feature point at each frame multiplied by the conversion factor and divided by the total number of frames. In the spirometry system, the imaging device may include a camera having at least a 30 frames per second rate. In the spirometry system, the ROI may comprise the shoulder.

In another aspect, the present disclosure provides a spirometry system comprising: an imaging device configured to capture images of a region of interest (ROI) in an upper body movement of a subject during inhalation and exhalation of a subject; and at least one controller in signal communication with the imaging device. The at least one controller is configured to: receive signals transmitted by the imaging device wherein the signals are representative of the captured images, process the received images, and determine an image-basest flow-volume curve for the subject by producing a calibration curve. In the spirometry system, producing the calibration curve can include converting the received images of the upper body of the subject into breathing volume. In the spirometry system, producing the calibration curve can include fitting a 5th order polynomial to multiple breathing cycles of the subject. In the spirometry system, the at least one controller can be configured to convert the calibration curve into the image-based flow-volume curve. In one version, the spirometry system does not include a device comprising any of a pressure transducer, an ultrasonic receiver, a water gauge, a mouthpiece, or a nose piece.

In another aspect, the present disclosure provides a spirometry system comprising: an imaging device configured to capture images of a region of interest (ROI) in an upper body movement of a subject during inhalation and exhalation of a subject: and at least one controller in, signal communication With the imaging device. The at least one controller is configured to: receive signals transmitted by the imaging device wherein the signals are representative of the captured images, process the received images, and determine an image-based spirometry parameter for the subject. In the spirometry system, the spirometry parameter may include a plurality of parameters, the plurality of parameters including at least one of (i) forced expiratory volume in the first second ("FEV1"), (ii) forced vital capacity ("FVC"), or (iii) peak expiratory flow rate ("PEF"). In one version, the spirometry system does not include a device comprising any of a pressure transducer, an ultrasonic receiver, a water gauge, a mouthpiece, or a nose piece.

In accordance with another aspect of the disclosure, a spirometry method includes capturing upper body movement images of a subject during inhalation and exhalation of the subject. The method further includes determining, based upon the captured images, at least one of an image-based flow-volume spirometry curve for the subject or an image-based spirometry parameter for the subject.

DETAILED DESCRIPTION

The following systems and methods address one or more of the aforementioned problems and provide additional advantages. As will be described herein, image-based spirometry systems and methods are provided. In one aspect, the systems and methods perform spirometry using an imaging device and determine a flow-volume (spirometry) curve and/or spirometry parameters, including forced expiratory volume in the first second ("FEV1"), forced vital capacity ("FVC"), and peak expiratory flow rate ("PEF") (or any combination or ratio thereof, such as the FEV1/FVC ratio or Tiffeneau-Pinelli index) to help diagnose and manage respiratory ailments such as asthma and COPD. As persons of ordinary skill in the art will recognize and appreciate, FEV1 is a measurement of the maximum amount of air a subject can forcefully exhale in one second. As persons of ordinary skill in the art will recognize and appreciate, FVC is a measurement of the total amount of air that a subject can forcibly exhale from the lungs after taking the deepest breath the subject is able to take. As persons of ordinary skill in the art will recognize, PEF is a measurement of a subject's maximum speed of expiration. Comparisons and calibrations of the image-based non-contact spirometry can be made with traditional or conventional spirometry devices or spirometers.

Figure 1:
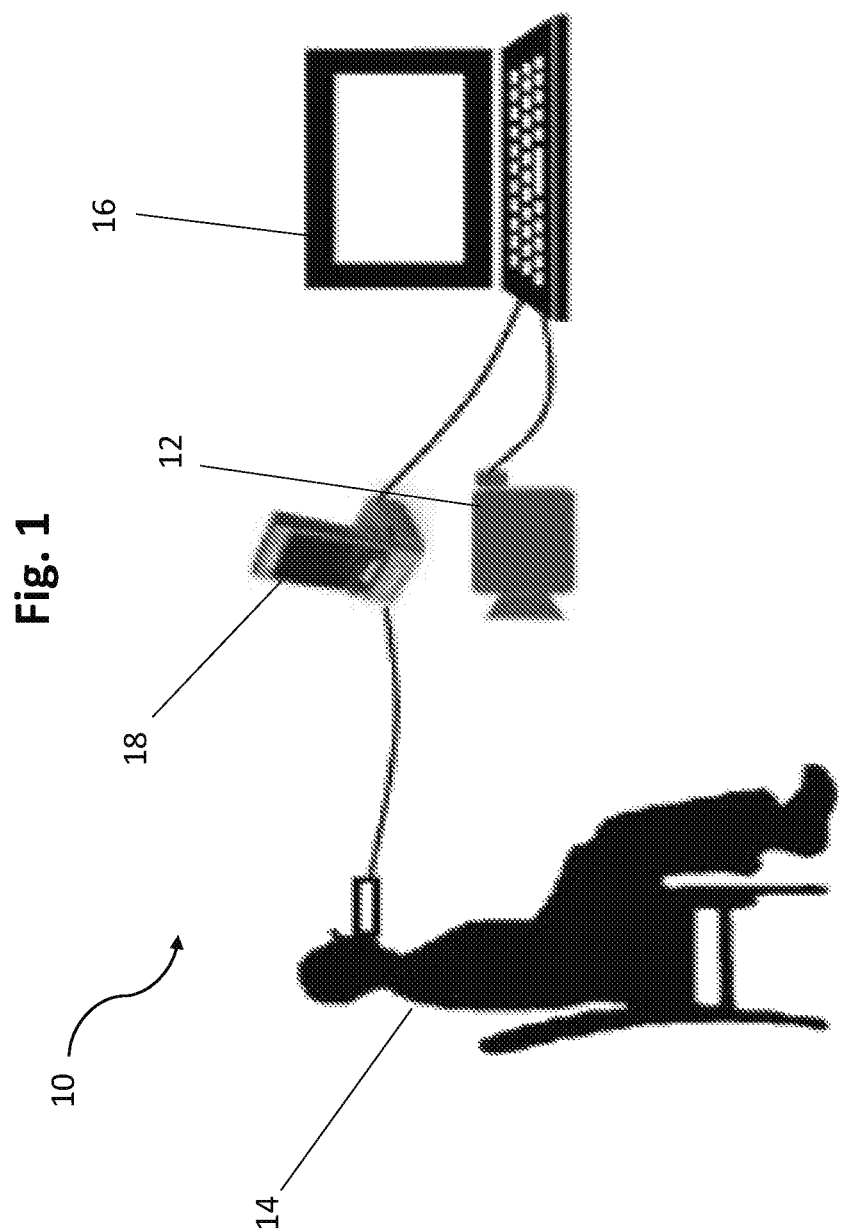
FIG. 1 illustrates an embodiment of a spirometry system of the present disclosure.

FIG. 1 illustrates one non-limiting embodiment of a spirometry system 10 of the present disclosure. Spirometry system 10 includes an imaging device 12 (e.g., a camera or web camera) configured to capture upper body movement of a subject 14 during inhalation and exhalation of the subject (e.g., facial and/or shoulder movement). At least one controller or computer 16 receives the captured images and is configured or programmed to analyze the upper body movement images, and determine a flow-volume curve for the subject and/or spirometry parameters such as FEV1, FVC and PEF. For comparison purposes, a traditional spirometry test can be performed simultaneously with the camera or image-based spirometry by utilizing a conventional spirometer or spirometer device 18 that communicates with the at least one controller or computer 16. The data from the image-based and traditional spirometry tests can be compared and used to construct a calibration curve for the subject. From the calibration curve, an exhalation volume can be determined from the subject's 14 upper body movement (e.g., shoulder movement), and a corresponding exhalation rate can be obtained, which in one example can be obtained via a time derivative of the exhalation volume. It should be appreciated that the at least one controller or computer 16 can include one or more processor, display, user interface such as a keyboard, mouse, or touch screen, and at least one memory device storing a plurality of instructions that when executed by the processor cause the system to carry out one or more functions of the system, such as processing signals and determining a spirometry flow-volume curve or spirometry parameters for the subject. The controller 16 in an embodiment can also inform the user how to use the system properly, whether the system is being used correctly, and if the system is not being used correctly, how to improve use of the system. For example, the system can provide audio and/or visual biofeedback to the user via the controller operating with at least one display device, which can include an audio component.

Figure 2:
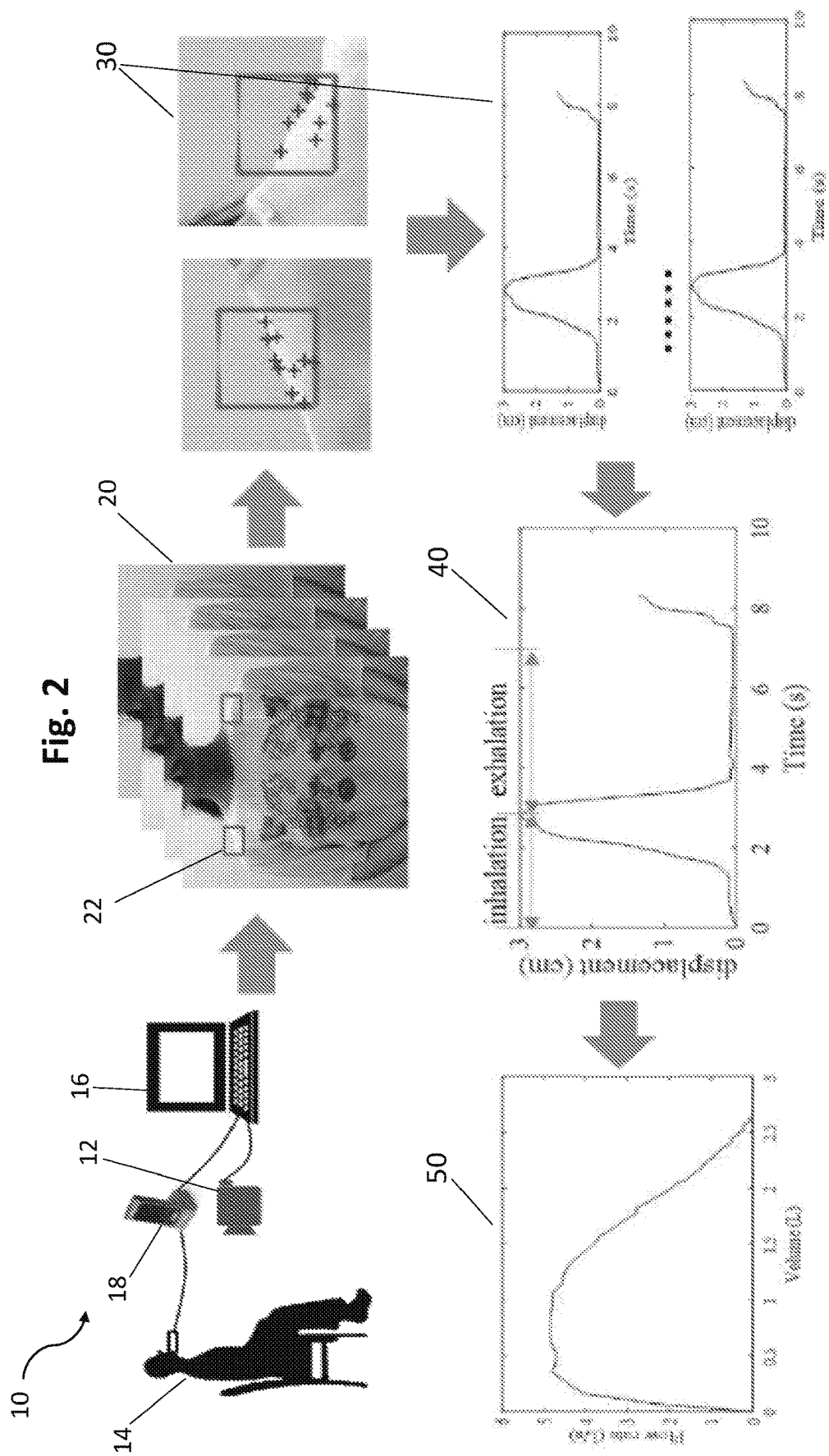
FIG. 2 illustrates a general schematic of one implementation of the system of FIG. 1 in which images that are captured of the subject's upper body are used to determine an image-based flow-volume spirometry curve and spirometry parameters.

FIG. 2 illustrates a general schematic of one implementation of the imaging-based spirometry system 10 in which the images of the subject's 14 upper body are captured via imaging device 12, and the images are used to determine, for example, a flow-volume (spirometry) curve and/or spirometry parameters, including forced expiratory volume in the first second ("FEV1"), forced vital capacity ("FVC"), and/or peak expiratory flow rate ("PEF"). In particular, FIG. 2 illustrates spirometry system 10 capturing images 20 of a subject's 14 upper body, namely a shoulder region 22 of the subject 14. The system performs video analysis 30 of the captured images and signal analysis 40 to determine a flow-volume or image-based spirometry curve 50. The video analysis 30 utilizes feature points of the shoulder region 22 of subject 14, and a displacement or change in position of the shoulder over time can be determined, as shown via the displacement versus time curve. The system 10 can perform signal analysis 40 to determine inhalation versus exhalation for the subject, and determine a flow rate versus volume spirometry curve 50 for same.

In one example implementation of the present disclosure, a web camera (e.g., Logitech C905) was used to capture data (e.g., video or images or other data representative thereof) of the subject's 14 upper body under typical indoor ambient light condition. The subject 14 was instructed to sit on a backrest chair at a distance of 90 cm from the camera and to perform a forced spirometry test using a gold standard commercial spirometer (e.g., MicroLoop, Carefusion), during which both the video and spirometry data were recorded synchronously with a laptop computer. The frame rate of the camera was set at 30 frames per second (fps), and the spatial resolution of frame was 960*720 pixels. The commercial spirometer complied with ATS/ERS 2005 standards, and its sampling rate was >100 Hz. It should be appreciated that the imaging device frame rate and spirometer device sampling rate can be any suitable rates for determining spirometry data of the subject. Having faster camera rates can improve the temporal resolution, and lead to more accurate measurements of the exhalation rate.

Sixteen subjects were tested, which included different genders (nine males, seven females), ages (28.1±3.2 years old, mean±SD), body mass indexes (22.5±3.6, mean±SD), and heights (1.71±0.09 m, mean±SD). Each of the sixteen subjects performed a standard forced spirometer procedure, and following that procedure were asked to wear a nose clip, inhale as deeply as possible, and exhale as hard as possible into a mouthpiece attached to the conventional spirometer device for as long as possible (forced inhalation and exhalation). In each test, the subject performed six forced breathing cycles continuously, in which three of the forced cycles were used to build calibration curves while the others were used for validation.

Two shoulder regions of each subject, consisting of 50 by 50 pixels each, were selected for detecting respiratory related movement. The regions included the middle portions of the shoulder region with clear boundaries that separated the body and background. The upper body movement of the subject was tracked with the Kanade-Lucas-Tomasi (KLT) tracker in the defined region of interest (ROI) (Lucas and Kanade 1981. Tomasi and Kanade 1991, Shi and Tomasi 1994) during the spirometry test. A Harris corner detector was used to detect feature points within the ROI of the shoulders. The detector computes the spatial variation (E) of image intensity in all directions, with equation (1) below:

$$E(u, v) = [u\ v] \begin{bmatrix} \langle I_x^2 \rangle & \langle I_x I_y \rangle \\ \langle I_x I_y \rangle & \langle I_y^2 \rangle \end{bmatrix} \begin{bmatrix} u \\ v \end{bmatrix}$$

where Ix, Iy are the gradients of the image intensity of the feature point in x and y directions, u, v are the numbers of pixels shifted from each point in the image in x and y directions, and the angle brackets, < > denotes averaging (over u, v). The matrix in Eq. (1) is the Harris matrix. The points, which have large eigenvalues in the Harris matrix, were defined as feature points.

To track the feature points frame by frame, affine transformation was used in the adjacent frames for ROI registration. In general, an affine transformation is composed of rotation, translation, scaling and skewing. Person of ordinary skill in the art will, after having reviewed and contemplated the teachings in this application, recognize that any subcombination of the forgoing movements may likewise be used for ROI registration. Considering two patches of an image in adjacent frames I, J, an affine map f acting on patch x is represented as equation (2) below, $$f(x) = Ax + b$$

where A is the deformation matrix, and b is the translation vector. The transformation parameters can be determined in a closed form when minimizing the dissimilarity measure, ε. An example of the dissimilarity measure is the sum of squared difference (SSD), given by equation (3) below, $$\varepsilon = \iint_w [J(Ax+b) - I(x)]^2 w(x) dx$$

where w is a weighting function.

To calibrate the shoulder movement, the number of pixels of a certain feature in the image frame were counted and related to the actual physical length of the feature. The conversion factor α is defined as equation (4) below, $$a = \frac{\text{feature\_length (mm)}}{\text{feature\_pixel\_number (pixel)}}$$

In the $i^{th}$ frame, the vertical component of the feature points, representing the shoulder position, pos, due to respiration, is given by equation (5) below, $$pos(i) = a \frac{1}{n} \sum_{j=1}^{n} y_j(i)$$

where $y_j(i)$ is the vertical component of j point in the $i^{th}$ frame, n is the total frame number of the video.

Figure 3:
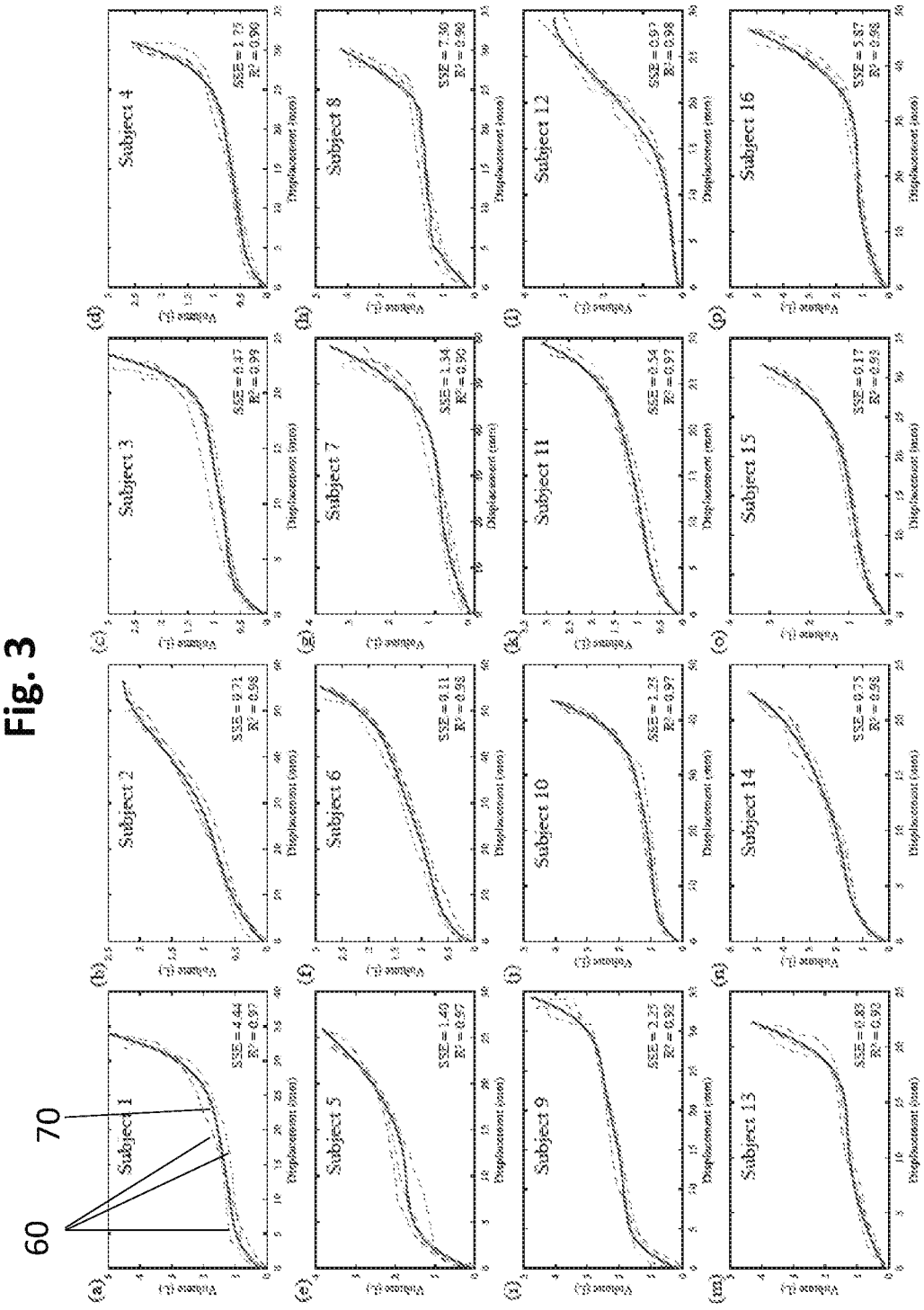
FIG. 3 illustrates randomly selected forced breathing cycles and calibration curves for sixteen subjects that performed one example implementation of the systems and methods of the present disclosure.

To correlate the shoulder displacement (change in position) with the spirometer reading, a calibration curve was determined for each subject, which converted the shoulder displacement to breathing volume in forced spirometry, as illustrated at FIG. 3. In particular, FIG. 3 shows the sixteen subjects tested in which each of the dotted lines 60 represents three randomly selected forced breathing cycles for a particular subject, and each of the solid line 70 represents=the exhaled volume data from the three randomly selected forced breathing cycles fitted with a 5th order polynomial for a particular subject. The sampling rate of the spirometer device set (>100 Hz) higher than the imaging device or web camera (30 Hz). Volume data was down sampled from the spirometer for close comparison. The flow rate was determined from the time derivative of the breathing volume.

In each test, the subject performed six forced breathing cycles continuously. Three forced cycles were randomly selected to build a calibration curve, and the other three cycles were used for validation for each subject. FIG. 3 plots the calibration curves for the sixteen different subjects. Despite the variability in the calibration curves for different subjects, each could be fitted with a 5th order polynomial using summed square of residuals ($SS_{res}$) and R-square ($R^2$) to evaluate the goodness of fit. $SS_{res}$ is defined as equation (6) below, $$SS_{res} = \sum_{j=1}^{n}(y_i - f_i)^2$$

where $y_i$ is the exhaled volume from the images, $f_i$ is the fitting function (5th order polynomial), and R-squared is defined by equation (7) below, $$R^2 = 1 - \sum_{i=1}^{n}(y_i - f_i)^2 \Big/ \sum_{i=1}^{n}(y_i - \bar{y})^2$$

where $\bar{y}$ is the average volume, and $\sum_{i=1}^{n}(y_i - \bar{y})^2$ is the total variance of the total variance of the data. $SS_{res}$ measures the variance of the fitting model, $R^2$ and describes how close the data are to the fitted curve. The $SS_{res}$ ranges from 0.11 to 7.30, with the median value of 1.10, indicating small errors between the exhaled volume using our proposed method and the tilting model in most cases. $R^2$ ranges from 0.90 to 0.99, indicating good fitting quality.

Figure 4:
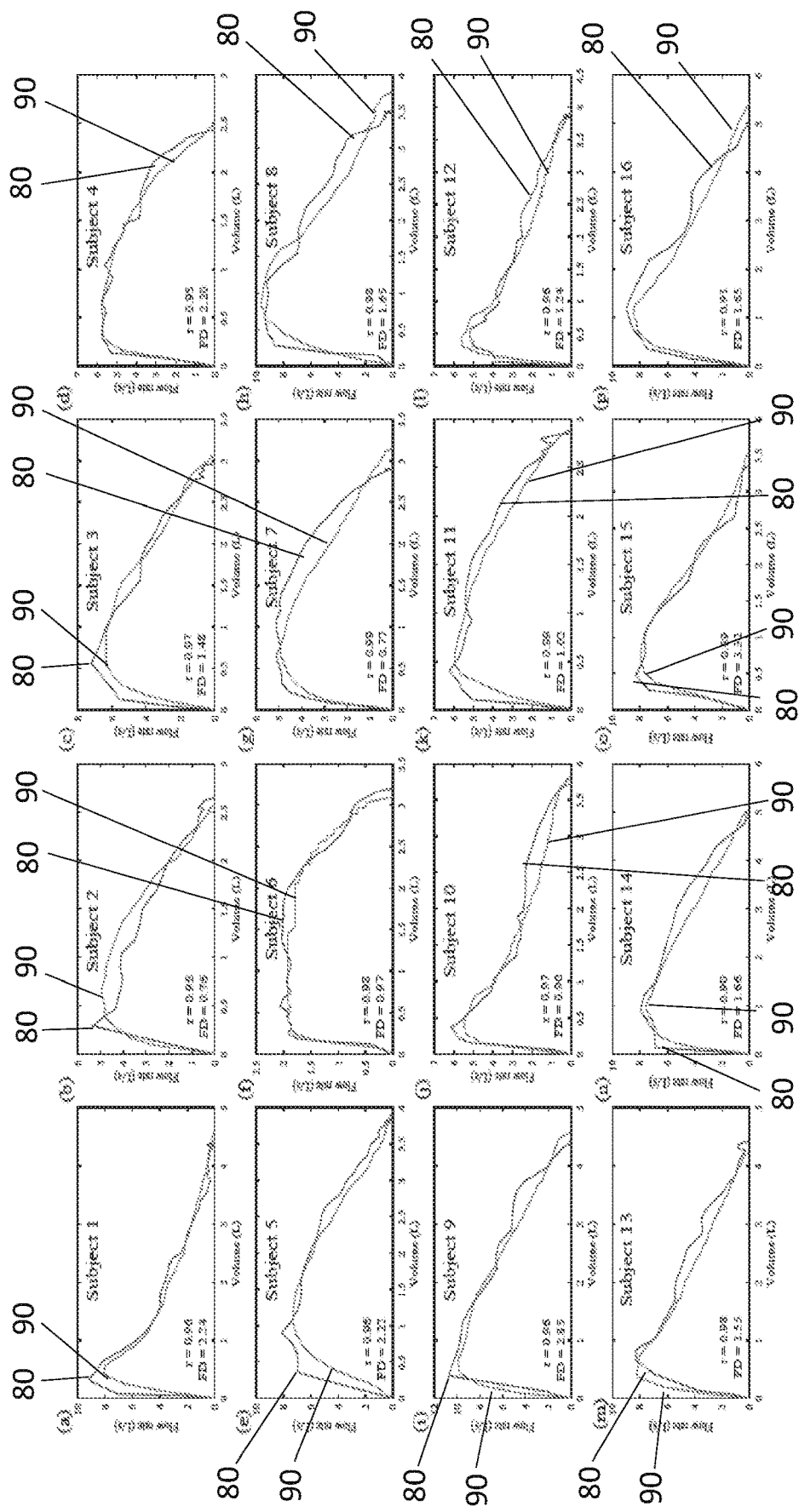
FIG. 4 illustrates flow-volume curves for the sixteen subjects that performed one example implementation of the systems and methods of the present disclosure.

Referring now to FIG. 4, using the calibration curves obtained above, the remaining three breathing cycles were converted into flow-volume curves 80 for each subject. For comparison, simultaneously recorded curves 90 from the commercial spirometer device are also shown in FIG. 4. Frechet distance (FD) and Pearson product-moment correlation coefficient (Parson's r) were used to measure the similarity between the image-based spirometry curves and the gold standard or spirometer device curves. Given two curves f:[a, b]→V and g: [a, b]→V. Frechet distance is defined as equation (8) below, $$F(f, g) = \inf_{\alpha, \beta t \in [0,1]} \max\{d(f(\alpha(t)) \cdot g(\beta(t)))\}$$

where α (resp. β) is an arbitrary continuous non-decreasing, function from [0,1] onto [a, b] (resp. [a', b']).

Pearson's r measures the linear dependence between the imaging-based and the gold standard spirometry results. As shown in FIG. 4, the Pearson r values ranged from 0.89 to 0.99, and FD was found to range from 0.76 to 3.32, indicating good agreements between the imaging-based and traditional spirometer curves for most subjects.

Figure 5:
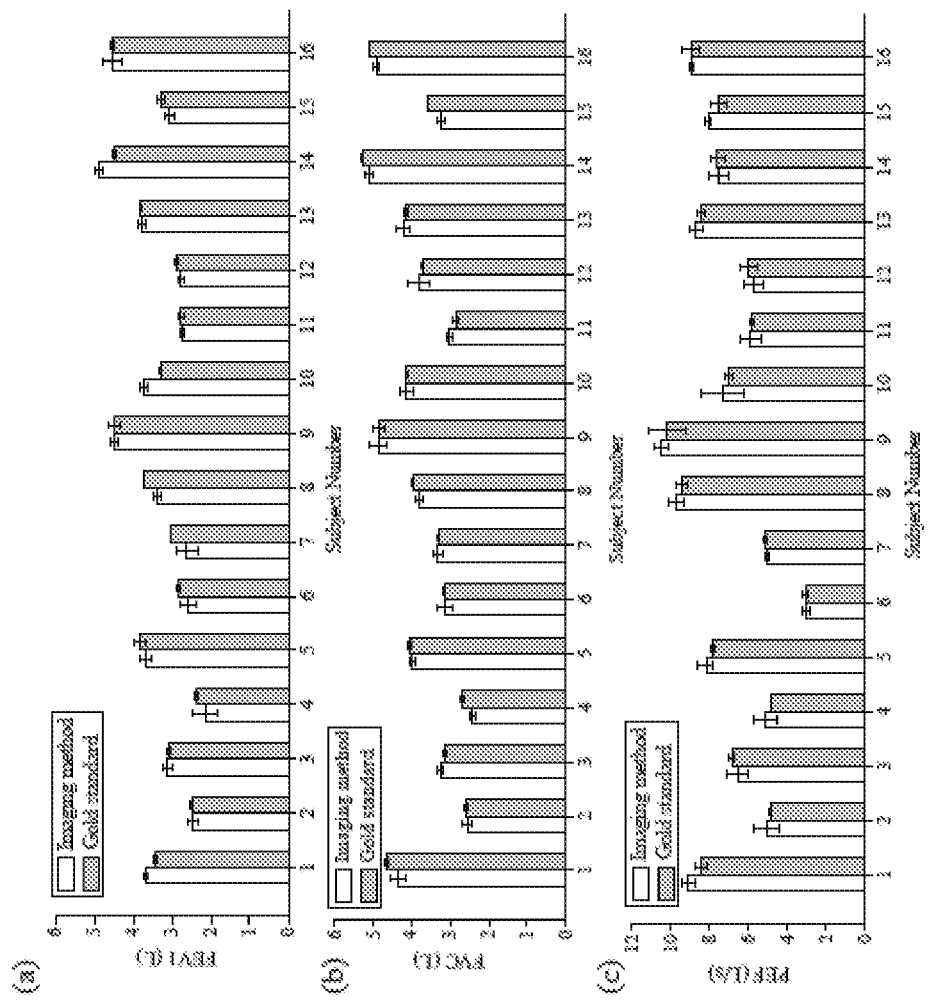
FIG. 5 illustrates image-based spirometry parameters and conventional spirometer parameters obtained for the sixteen subjects that performed one example implementation of the systems and methods of the present disclosure.

Vital parameters such as FEV1, FVC and PE were determined from the imaging-based spirometry curves. FIG. 5 and Table 1 below shows that the results from the image-based method are in close agreement with those determined by the gold standard spirometer device (FIG. 5). To quantify the agreement, the Pearson r, root-mean-square-error (RMSE) and paired sample test were analyzed. The Pearson r values for FEV1, FVC and PEF are 0.95, 0.98 and 0.97 respectively, indicating good linear correlation between the imaging based and traditional spirometers. The RMSE values of FEV1, FVC and PEF are 0.27, 0.18 and 0.56 respectively, indicating small differences between the two methods. In the paired t-test, FEV1 and FVC show the pairwise difference between the imaging-based spirometry and the gold standard spirometry with a mean of zero at the 5% significance level, which is consistent with the RMSE values.

TABLE 1

| subject | FEV1 (L) | | FVC (L) | | PEF (L/s) | |
|---|---|---|---|---|---|---|
| | Imaging | Gold | Imaging | Gold | Imaging | Gold |
| 1 | 3.69 ± 0.06 | 3.43 ± 0.04 | 4.34 ± 0.21 | 4.63 ± 0.06 | 9.07 ± 0.32 | 8.42 ± 0.31 |
| 2 | 2.46 ± 0.12 | 2.50 ± 0.01 | 2.55 ± 0.12 | 2.59 ± 0.04 | 5.03 ± 0.65 | 4.86 ± 0.07 |
| 3 | 3.11 ± 0.12 | 3.09 ± 0.04 | 3.25 ± 0.08 | 3.12 ± 0.06 | 6.55 ± 0.57 | 6.86 ± 0.11 |
| 4 | 2.14 ± 0.33 | 2.38 ± 0.03 | 2.42 ± 0.07 | 2.69 ± 0.04 | 5.10 ± 0.57 | 4.80 ± 0.03 |
| 5 | 3.67 ± 0.14 | 3.84 ± 0.14 | 3.98 ± 0.07 | 4.03 ± 0.03 | 8.16 ± 0.40 | 7.80 ± 0.12 |
| 6 | 2.59 ± 0.19 | 2.83 ± 0.06 | 3.14 ± 0.22 | 3.14 ± 0.03 | 3.01 ± 0.20 | 3.07 ± 0.16 |
| 7 | 2.62 ± 0.28 | 3.04 ± 0.01 | 3.32 ± 0.12 | 3.31 ± 0.03 | 5.01 ± 0.13 | 5.14 ± 0.13 |
| 8 | 3.37 ± 0.09 | 3.73 ± 0.02 | 3.80 ± 0.09 | 3.95 ± 0.15 | 9.71 ± 0.36 | 9.40 ± 0.30 |
| 9 | 4.46 ± 0.10 | 4.47 ± 0.16 | 4.86 ± 0.22 | 4.85 ± 0.04 | 10.46 ± 0.34 | 10.16 ± 0.95 |
| 10 | 3.73 ± 0.12 | 3.30 ± 0.02 | 4.12 ± 0.16 | 4.11 ± 0.07 | 7.30 ± 1.07 | 7.02 ± 0.21 |
| 11 | 2.74 ± 0.05 | 2.75 ± 0.07 | 3.01 ± 0.09 | 2.85 ± 0.02 | 5.90 ± 0.55 | 5.81 ± 0.11 |
| 12 | 2.76 ± 0.09 | 2.86 ± 0.06 | 3.80 ± 0.26 | 3.71 ± 0.04 | 5.67 ± 0.49 | 6.00 ± 0.44 |
| 13 | 3.78 ± 0.08 | 3.81 ± 0.02 | 4.21 ± 0.18 | 4.14 ± 0.02 | 8.67 ± 0.32 | 8.40 ± 0.17 |
| 14 | 4.88 ± 0.12 | 4.46 ± 0.05 | 5.07 ± 0.10 | 5.24 ± 0.01 | 7.55 ± 0.49 | 7.60 ± 0.37 |
| 15 | 3.07 ± 0.13 | 3.28 ± 0.10 | 3.23 ± 0.10 | 3.57 ± 0.01 | 8.06 ± 0.18 | 7.49 ± 0.38 |

It should be appreciated from the foregoing that accurate spirometry can be obtained from shoulder displacement alone without complex three-dimensional chest movement measurements. In image-based spirometry according to aspects of the present disclosure, accurate tracking of shoulder displacement helps ensure accurate spirometry parameters and curves. A KLT tracking algorithm, which uses clear contrast of shoulder images, can be used in one aspect of the present systems and methods. The subject's clothes in one implementation can have substantially different color from the background color.

It should additionally be appreciated that the systems and methods of the present disclosure can determine spirometry curves and important respiratory parameters for a subject, including FEV1, FVC and PEF, using an image-based approach, which parameters are in close agreement with those of conventional spirometer devices and methods. The image-based spirometry systems and methods herein therefore do not require a spirometer device, a mouthpiece or a nose clip, which can lower the cost and improve user experience, thus contributing to the diagnosis and management of a large and growing asthma and COPD populations. Thus, in certain embodiments, the system does not include one or more of a physical spirometer device (e.g., a device comprising one or more of a pressure transducer, an ultrasonic transmitter and/or receiver, or a water gauge), a mouthpiece, or a nose piece.

In certain embodiments, a spirometry method comprises a step of capturing images of a region of interest (ROI) in an upper body movement of a subject during inhalation and exhalation of the subject. The method further comprises determining, based upon the captured images, at least one of (i) an image-based flow-volume curve for the subject or (ii) an image-based spirometry parameter for the subject. In certain embodiments, the method may further comprise diagnosing the subject as having an obstructive and/or restrictive lung disease based on the image-based flow-volume curve or image-based spirometry parameter. In certain embodiments, the method may further comprise administering to the subject a treatment for the obstructive and/or restrictive lung disease based on the image-based flow-volume curve or image-based spirometry parameter.

While certain embodiments have been shown and described herein, it will be obvious to those skilled in the art that such embodiments are provided by way of example only. Numerous variations, changes, and substitutions will now occur to those skilled in the art without departing from the scope of the technologies disclosed herein. It should be understood that various alternatives to the embodiments of the technologies described herein may be employed. It is intended that the following claims define the scope of the invention and that methods and structures within the scope of these claims and their equivalents be covered thereby.

What is claimed is:

1. A spirometry system, comprising:
   an imaging device configured to capture images of a region of interest (ROI) in an upper body movement of a subject during inhalation and exhalation of a subject; and
   at least one controller in signal communication with the imaging device configured to:
   receive signals transmitted by the imaging device, the signals being representative of the captured images,
   process the received images, and
   determine an image-based flow-volume curve for the subject by:
   (i) identifying feature points in the ROI;
   (ii) registering adjacent frames in the ROI;
   (iii) determining transformation parameters;
   (iv) calibrating the movement of the ROI; and
   (v) determining the position of the ROI in a selected frame due to respiration as a function of a vertical component of the feature points in each frame, wherein step (iv) comprises calibrating the movement by determining a ratio of a length of an identified feature point to a number of pixels corresponding to the feature point.

2. The spirometry system of claim 1, wherein step (i) comprises using a Harris corner detector to identify the feature points.

3. The spirometry system of claim 1, wherein step (ii) comprises applying affine transformation to adjacent frames in the received images.

4. The spirometry system of claim 3, wherein step (iii) comprises acquiring the transformation parameters from a vector produced by the affine transformation.

5. The spirometry system of claim 1, wherein step (v) comprises calculating a summation of the vertical points of a feature point at each frame multiplied by the conversion factor and divided by the total number of frames.

6. The spirometry system of claim 1, wherein the imaging device includes a camera having at least a 30 frames per second rate.

7. The spirometry system of claim 1, wherein the ROI comprises the shoulder.

8. A spirometry system, comprising:
   an imaging device configured to capture images of a region of interest (ROI) in an upper body movement of a subject during inhalation and exhalation of a subject, and
   at least one controller in signal communication with the imaging device configured to:
   receive signals transmitted by the imaging device, the signals being representative, of the captured images,
   process the received images, and
   determine an image-based flow-volume curve for the subject by producing a calibration curve, wherein the controller is configured to convert the calibration curve into the image-based flow-volume curve.

9. The spirometry system of claim 8, wherein producing the calibration curve includes fitting a 5th order polynomial to multiple breathing cycles of the subject.

10. The spirometry system of claim 9, wherein the system does not include a device comprising any of a pressure transducer, an ultrasonic receiver, a water gauge, a mouthpiece, or a nose piece.

11. A spirometry system, comprising:
    an imaging device configured to capture images of a region of interest (ROI) in an upper body movement of a subject during inhalation and exhalation of a subject, and
    at least one controller in signal communication with the imaging device configured to:
    receive signals transmitted by the imaging device, the signals being representative, of the captured images,
    process the received images, and
    determine an image-based flow-volume curve for the subject by producing a calibration curve
    wherein producing the calibration curve includes converting the received images of the upper body of the subject into breathing volume.

* * * * *